US00PP34468P2

(12) United States Plant Patent
Mathey

(10) Patent No.: US PP34,468 P2
(45) Date of Patent: Aug. 2, 2022

(54) ***HYDRANGEA* PLANT NAMED 'SMNHPSB'**

(50) Latin Name: *Hydrangea paniculata*
Varietal Denomination: 'SMNHPSB'

(71) Applicant: Spring Meadow Nursery Inc., Grand Haven, MI (US)

(72) Inventor: Megan Mathey, Holland, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/483,212

(22) Filed: Sep. 23, 2021

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct cultivar of *Hydrangea* plant named 'SMNHPSB' is disclosed, characterized by large, mophead inflorescences with pure white sepals that progress to brilliant dark pink/pinkish-red. Plants have dwarf habits and dark green foliage with pronounced venation. The new variety is a *Hydrangea*, typically produced as an outdoor ornamental plant.

3 Drawing Sheets

Latin name of the genus and species: *Hydrangea paniculata.*

Variety denomination: 'SMNHPSB'.

BACKGROUND OF THE INVENTION

The new cultivar is a product of a planned breeding program conducted by the inventor, at a commercial nursery in Grand Haven, Mich. The objective of the breeding program was to produce new *Hydrangea* varieties with dwarf habits and good foliage. The open-pollination resulting in the new variety was made during the Summer of 2013.

The seed parent is an unnamed, unpatented dwarf *Hydrangea paniculata*. The pollen parent cannot be identified as this new selection resulted from an open-pollination.

The new variety was found and selected by the inventor in the Summer of 2015 at the same nursery in Grand Haven, Mich.

Asexual reproduction of the new cultivar 'SMNHPSB' was first performed during 2015 in Grand Haven, Mich., by softwood cuttings. Through subsequent asexual propagation, multiple additional generations have been reproduced, having shown that the unique features of this cultivar are stable and reproduced true to type.

SUMMARY OF THE INVENTION

The cultivar 'SMNHPSB' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHPSB'. These characteristics in combination distinguish 'SMNHPSB' as a new and distinct *Hydrangea* cultivar:

1. Very dwarf habit.
2. Thick, coarse-textured leaves with pronounced venation.
3. Dense branching.
4. Dark green foliage.
5. Large, rounded to conical-shaped mophead inflorescences.
6. Pure white sepals fade to dark pink, pinkish-red.

PARENT COMPARISON

Plants of the new cultivar *Hydrangea* 'SMNHPSB' can be compared to the seed parent, an unnamed, unpatented dwarf *Hydrangea paniculata*. Plants of 'SMNHPSB' are similar to plants of the seed parent in most horticultural characteristics, however, plants of 'SMNHPSB' differ in the following:

1. Inflorescences of 'SMNHPSB' have abundant infertile flowers (mophead), while inflorescences of the seed parent have fewer infertile flowers (lacecap).

COMMERCIAL COMPARISON

Plants of the new cultivar *Hydrangea* 'SMNHPSB' can be compared to the commercial variety *Hydrangea* 'SMNHPK', U.S. Plant Pat. No. 32,512. Plants of 'SMNHPSB' are similar to plants of 'SMNHPK' in most horticultural characteristics, however, plants of 'SMNHPSB' differ in the following:

1. 'SMNHPSB' has coarse-textured, thick leaves, while 'SMNHPK' has less thick, coriaceous leaves.
2. 'SMNHPSB' has ovate-shaped leaves with acute tips, while 'SMNHPK' has more elliptical leaves with acuminate tips.
3. 'SMNHPSB' has less delicate looking sepals than 'SMNHPK'.

BRIEF DESCRIPTION OF THE PHOTOGRAPHS

'SMNHPSB' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Hydrangea*.

DETAILED BOTANICAL DESCRIPTION

Figure 1:
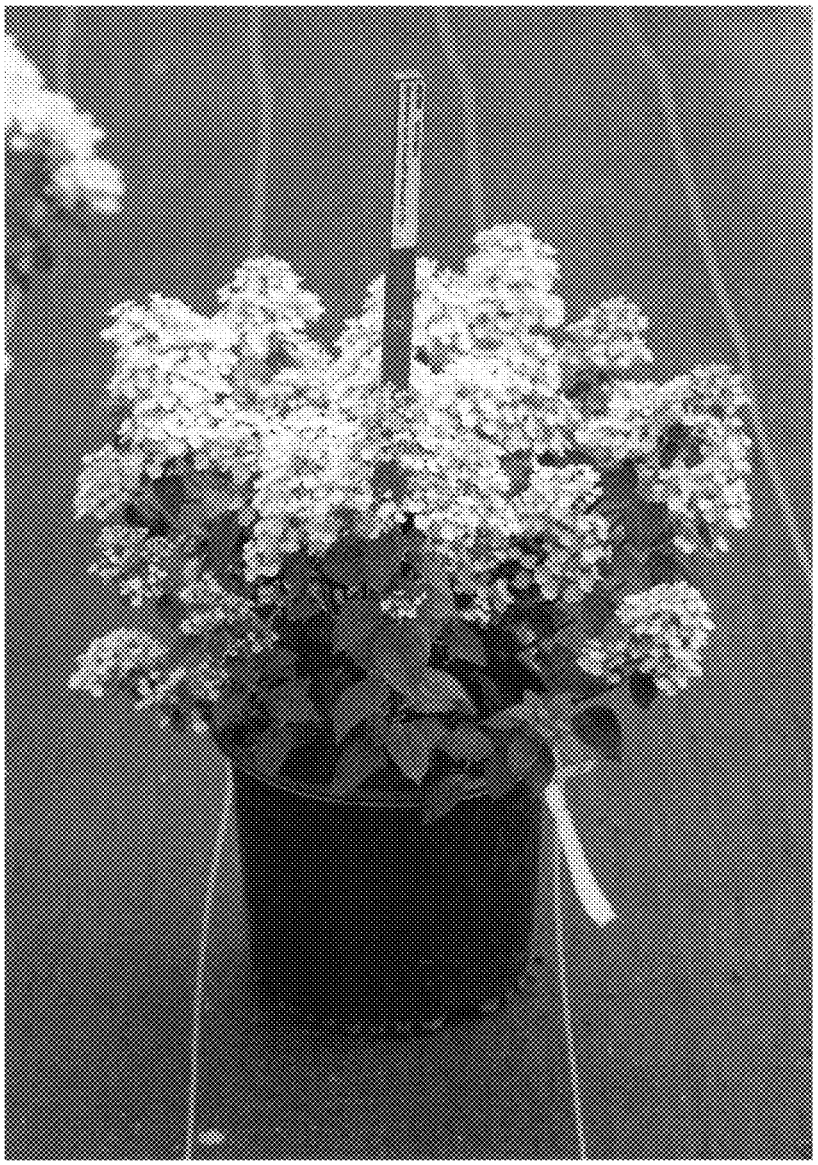
FIG. 1 shows a container grown plant of 'SMNHPSB' grown in a greenhouse in Grand Haven, Mich. at about 1.5 years of age.
Figure 2:
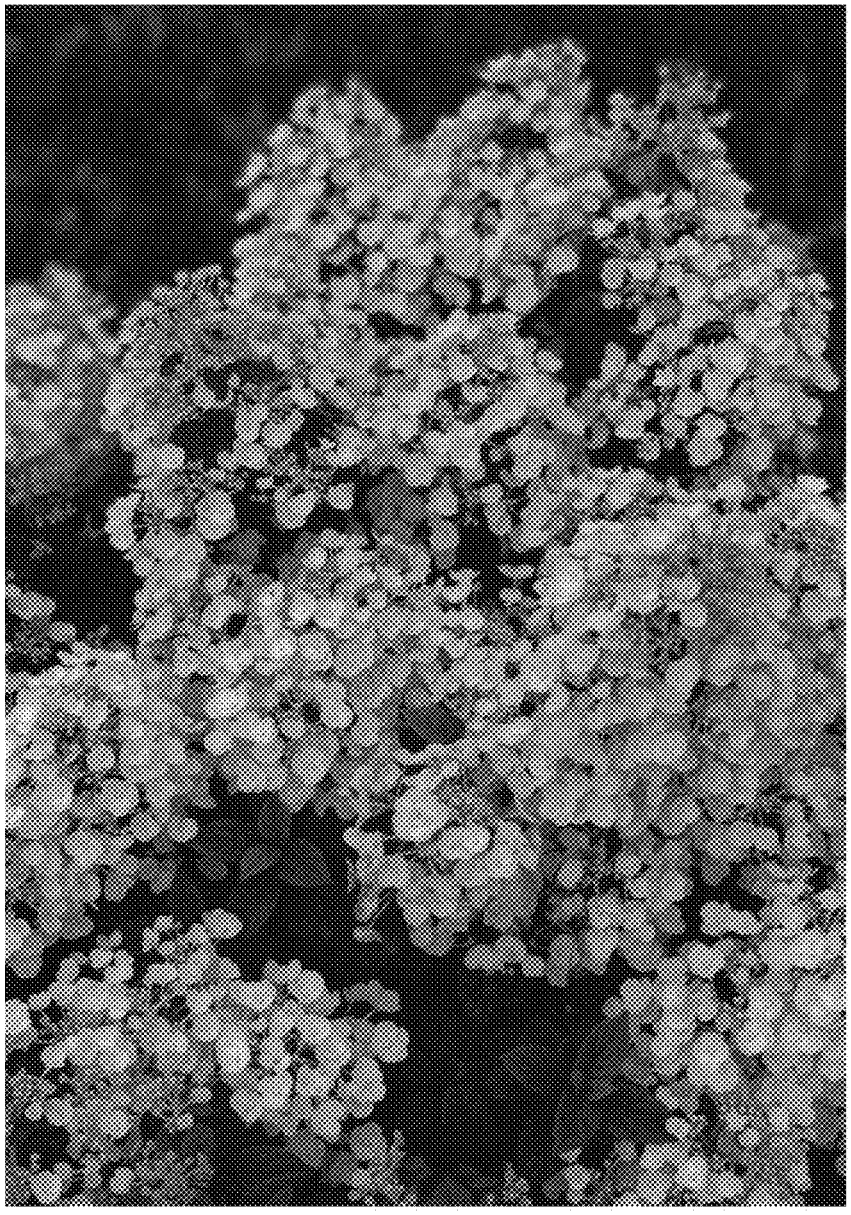
FIG. 2 shows the mature inflorescence of a container-grown plant of 'SMNHPSB', grown in a greenhouse in Grand Haven, Mich.
Figure 3:
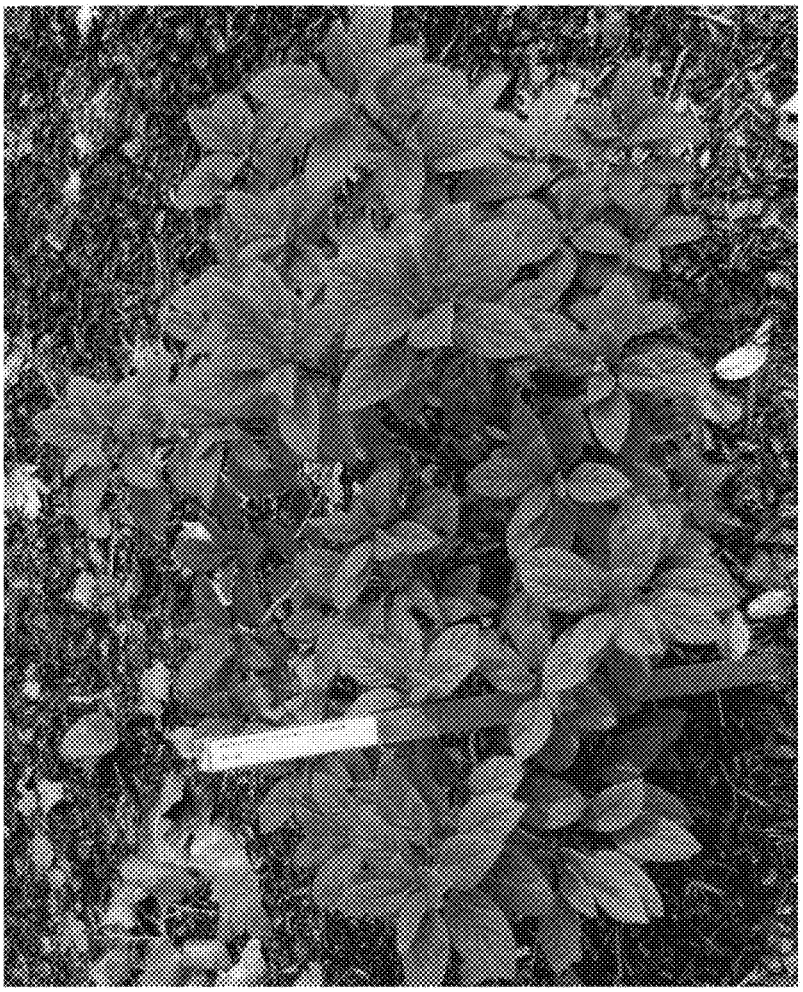
FIG. 3 shows a field grown plant of 'SMNHPSB' at approximately 2 years.

In the following description, color references are made to The Royal Horticultural Society Colour Chart 2015, except where general terms of ordinary dictionary significance are used. The following observations and measurements describe 'SMNHPSB' plants grown outdoors in Grand Haven, Mich. The plants were about 2 to 3 years old. Temperatures ranged from 5° C. to 10° C. at night to 18° C. to 27° C. during the day. No artificial light, photoperiodic treatments were given to the plants. Measurements and numerical values represent averages of typical plant types. Botanical classification: *Hydrangea paniculata* 'SMNHPSB'.

PROPAGATION

Typical method: Softwood cuttings.
Root initiation: Approximately 18 days.
Time to produce rooted cutting: 90 days.
Roots: Medium thickness, freely branching, fibrous, dense. Creamy white to brown in color, not accurately measured with R.H.S. chart.

PLANT

Growth habit: Upright, rounded, mostly upwards.
Height: 47 cm.
Plant spread: 70 cm.
Pot size of plant described: 3 gallon container.
Age of plant described: Approximately 2 to 3 years.
Growth rate: Slow to moderate.
Plant vigor: Good.
Stem:
- *Branching*.—Basal.
- *Number of lateral branches*.—15.
- *Shape*.—Round.
- *Color*.—Immature: RHS Yellow-Green 145A, some with tinges of Greyed-Orange 177C, and Yellow-White 158B lenticels. Mature: RHS Greyed-Orange 177A to Grey-Brown N199B.
- *Length*.—40 cm.
- *Width*.—5 mm.
- *Aspect*.—60 to 80°.
- *Strength*.—Strong.
- *Pubescence*.—None.
- *Internode length*.—2.5 to 4 cm.

FOLIAGE

Leaf:
- *Arrangement*.—Opposite.
- *Shape*.—Ovate.
- *Length*.—6.5 cm.
- *Width*.—3.5 cm.
- *Apex*.—Acute.
- *Base*.—Obtuse.
- *Margin*.—Serrulate.
- *Texture of top surface*.—Coarse, with fine hairs and pronounced venation.
- *Texture of bottom surface*.—Coarse, with fine hairs along veins and mid-rib.
- *Pubescence*.—On both sides.
- *Color*.—Young foliage upper side: RHS Yellow-Green 146B. Young foliage under side: Near RHS Yellow-Green 146C. Mature foliage upper side: RHS Green 137B. Mature foliage, under side: RHS Yellow-Green 147B.

Venation:
- *Type*.—Pinnate.
- *Color*.—Upper side: RHS Yellow-Green 147B. Under side: RHS Yellow-Green 147B.

Petiole:
- *Length*.—1 cm.
- *Width*.—2 mm.
- *Color*.—Upper side: RHS Yellow-Green 147B, with tinges of Greyed-Orange 174A. Under side: RHS Yellow-Green 147B.
- *Texture*.—Upper side: Smooth, some slight pubescence. Under side: Smooth, some slight pubescence.

INFLORESCENCE

Natural flowering season: Summer.
Inflorescence type: Mophead.
Panicle:
- *Shape*.—Rounded to slightly cone-shaped.
- *Height*.—15 cm.
- *Diameter*.—13 cm.

Fragrance: None.
Sterile flowers:
- *Flowers per inflorescence*.—250 to 350.
- *Aspect*.—Upright and outward.
- *Shape*.—Round whorl.
- *Length*.—2 to 2.5 cm.
- *Diameter*.—2 to 2.5 cm.
- *Depth*.—3 mm.
- *Persistent or self-cleaning*.—Persistent.

Bud:
- *Length*.—2 mm.
- *Bud diameter*.—2 mm.
- *Bud shape*.—Obovate.
- *Bud color*.—RHS Green-White 157D.
- *Quantity per inflorescence*.—Average range at full opening of oldest flowers, 10 to 40.

Petals:
- *Number per flower*.—4 to 5.
- *Arrangement*.—Cruciform/stellate.
- *Shape*.—Ovate.
- *Tip*.—Acute.
- *Base*.—Obtuse.
- *Margin*.—Entire.
- *Length*.—2 mm.
- *Width*.—2 mm.
- *Texture*.—Upper side: Smooth. Under side: Smooth.
- *Color*.—When Opening, Upper side: RHS White 155A. When Opening, Under side: RHS White NN155B. Fully Opened, Upper side: RHS White 155A. Fully Opened, Under side: RHS White 155B.

Sepal:
*Number.*—4 to 5.
*Arrangement.*—Cruciform/whorl.
*Shape.*—Orbicular.
*Tip.*—Obtuse.
*Base.*—Obtuse.
*Margin.*—Entire.
*Length.*—1 cm.
*Width.*—1.25 mm.
*Texture.*—Upper side: Smooth with some venation. Under side: Smooth with some venation.
*Color.*—When Opening, Upper side: RHS White 155B, with tinges of Yellow-Green 144D. When Opening, Under side: RHS White 155B, with tinges of Yellow-Green 144D. Fully Opened, Upper side: RHS White 155B, with tinges of Yellow-Green 144D. Fully Opened, Under side: RHS White 155B, with tinges of Yellow-Green 144D. Fading, Upper side: RHS Greyed-Red 181B to 181C. Fading, Under side: RHS Greyed-Red 181B to 181C.

Pedicel:
*Length.*—1 cm.
*Diameter.*—2 mm.
*Angle.*—45°.
*Strength.*—Good, flexible.
*Texture.*—Smooth, somewhat pubescent.
*Color.*—RHS White 155B.

Fertile flowers:
*Flowers per inflorescence.*—Around 300.
*Aspect.*—Upright.
*Shape.*—Stellate.
*Length.*—6 mm.
*Diameter.*—6 mm.
*Depth.*—3 mm.
*Persistent or self-cleaning.*—Self-cleaning.

Bud:
*Length.*—2 mm.
*Bud diameter.*—2 mm.
*Bud shape.*—Obovate.
*Bud color.*—RHS Green-White 157D.
*Quantity per inflorescence.*—Average range at full opening of oldest flowers, 30 to 70.

Petals:
*Number per flower.*—5.
*Arrangement.*—Stellate/whorl.
*Shape.*—Ovate.
*Tip.*—Acute.
*Base.*—Obtuse.
*Margin.*—Entire.
*Length.*—2 mm.
*Width.*—2 mm.
*Texture.*—Upper side: Smooth. Under side: Smooth.
*Color.*—When Opening, Upper side: RHS White 155A. When Opening, Under side: RHS White NN155B. Fully Opened, Upper side: RHS White 155A. Fully Opened, Under side: RHS White NN155B. Fading, Upper side: RHS Greyed-Red 181B to 181C. Fading, Under side: RHS Greyed-Red 181B to 181C.

Sepal: None.

Pedicel:
*Length.*—1 mm.
*Diameter.*—1 mm.
*Angle.*—45°.
*Strength.*—Good.
*Texture.*—Smooth.
*Color.*—RHS White 155A.

REPRODUCTIVE ORGANS

Sterile flower:
Stamens:
*Number.*—10.
*Filament color.*—RHS White 155A.
*Filament length.*—1 mm.
Anthers:
*Length.*—About 1 mm.
*Shape.*—Rounded, globular.
*Color.*—RHS Yellow-White 158A.
*Pollen.*—Moderate.
*Pollen color.*—RHS Yellow-White 158A.
Pistil:
*Number.*—1.
*Length.*—2 mm.
Stigma:
*Shape.*—3-lobed.
*Color.*—RHS White 155A.
*Style length.*—About 1 mm.
*Style color.*—RHS White 155A.

Fertile flower:
Stamen:
*Number.*—10.
*Filament length.*—1 mm.
*Filament color.*—RHS White 155A.
Anther:
*Shape.*—Rounded, globular.
*Length.*—About 1 mm.
*Color.*—RHS White 158A.
*Pollen amount.*—Moderate.
*Pollen color.*—RHS Yellow-White 158A.
Pistil:
*Number.*—1.
*Length.*—2 mm.
Stigma:
*Shape.*—3-lobed.
*Color.*—RHS White 155A.
*Style length.*—About 1 mm.
*Style color.*—RHS White 155A.

OTHER CHARACTERISTICS

Disease resistance: Neither resistance nor susceptibility to the normal diseases and pests of *Hydrangea* has been observed.

Drought tolerance and cold tolerance: The new cultivar can tolerate cold temperatures to approximately −32° C. and tolerates an upper temperature range to at least 36° C.

Fruit/seed production: Not observed to date.

What is claimed is:

1. A new and distinct cultivar of *Hydrangea* plant named 'SMNHPSB' as herein illustrated and described.

* * * * *